(12) United States Patent
Fujita et al.

(10) Patent No.: US 9,194,724 B2
(45) Date of Patent: Nov. 24, 2015

(54) GAS SENSOR

(71) Applicant: NGK SPARK PLUG CO., LTD., Nagoya-shi, Aichi-ken (JP)

(72) Inventors: Tomohisa Fujita, Iwakura (JP); Nobuhiro Inoue, Tajimi (JP); Makoto Kume, Inuyama (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 396 days.

(21) Appl. No.: 13/863,961

(22) Filed: Apr. 16, 2013

(65) Prior Publication Data

US 2013/0305809 A1 Nov. 21, 2013

(30) Foreign Application Priority Data

Apr. 17, 2012 (JP) .................... 2012-093779
Apr. 15, 2013 (JP) .................... 2013-084668

(51) Int. Cl.
*G01D 11/24* (2006.01)
*G01N 27/407* (2006.01)

(52) U.S. Cl.
CPC .......... *G01D 11/245* (2013.01); *G01N 27/4077* (2013.01)

(58) Field of Classification Search
CPC .. G01N 27/406; G01N 27/409; G01N 27/403
USPC ............................. 73/25.05, 31.05
See application file for complete search history.

(56) References Cited

U.S. PATENT DOCUMENTS

| | | | |
|---|---|---|---|
| 2005/0241937 A1* | 11/2005 | Shichida et al. | 204/424 |
| 2007/0251823 A1* | 11/2007 | Yamada | 204/424 |
| 2008/0028831 A1* | 2/2008 | Nakashima et al. | 73/31.05 |
| 2008/0067066 A1* | 3/2008 | Okumura et al. | 204/424 |
| 2008/0105037 A1* | 5/2008 | Nakashima et al. | 73/31.05 |
| 2011/0126610 A1 | 6/2011 | Sekiya et al. | |

FOREIGN PATENT DOCUMENTS

JP 2011-112557 A 6/2011

* cited by examiner

*Primary Examiner* — Hezron E Williams
*Assistant Examiner* — David Z Huang
(74) *Attorney, Agent, or Firm* — Sughrue Mion, PLLC (57) ABSTRACT

In a gas sensor (100), a base end portion (175b) of a second outer wall (175) of an outer protector (171) is airtightly connected to a forward end portion (164c) of a first inner wall (164) of an inner protector (161). The outer protector (171) has a taper wall (172) which is located on the axially forward end side of the second outer wall (175). The taper wall (172) has the shape of a tapered tube whose diameter decreases toward the axially forward end side, and has a second outer hole (176), which is a forward end opening. The entire taper wall (172) is disposed on the axially forward end side in relation to the inner bottom wall (162) of the inner protector (161).

8 Claims, 6 Drawing Sheets

GAS SENSOR

TECHNICAL FIELD

The present invention relates to a gas sensor including a detection element which is exposed to a gas-to-be-detected in order to detect a particular gas component contained in the gas, and more particularly to a gas sensor having a protector for protecting the detection element from adhesion of water or the like.

BACKGROUND ART

There has conventionally been known a gas sensor which is attached to an exhaust pipe of an automobile or the like for use and which includes a detection element which generates an electromotive force the magnitude of which changes in accordance with the concentration of a particular gas, such as $NO_x$ (nitrogen oxides) or oxygen, contained in exhaust gas, or whose resistance changes in accordance with the concentration of the particular gas. In such a gas sensor, if a water droplet contained in exhaust gas adheres to the detection element when heated to a high temperature, the detection element may suffer damage, such as cracking, due to thermal shock. Therefore, a protector for covering the detection element is attached to the gas sensor so as to protect the detection element from adhesion of water (see, for example, Patent Document 1).

PRIOR ART DOCUMENT

Patent Document

[Patent Document 1] Japanese Patent Application Laid-Open (kokai) No. 2011-112557

The gas sensor of Patent Document 1 includes a sensor element (detection element); a first protection cover (inner protector) which covers the sensor element and which has a first gas introduction hole for permitting a gas-to-be measured (gas-to-be-detected) to flow from the outside of the first protection cover to the inside thereof; a second protection cover (outer protector) which covers the first protection cover and which has a second gas introduction hole for permitting the gas-to-be measured to flow from the outside of the second protection cover to the inside thereof; and a gas flow passage which extends from the second gas introduction hole to the first gas introduction hole through a space between the first protection cover and the second protection cover, extends from the first gas introduction hole into the interior of the first protection cover, and reaches to a forward end of the sensor element.

Further, in the gas sensor of Patent Document 1, at least one of the first protection cover and the second protection cover has an inner wall member which is solid or has a closed space therein and which is disposed to reduce the width of at least a portion of a flow passage which is a portion of the gas flow passage and which extends from the second gas introduction hole to the first gas introduction hole.

SUMMARY OF THE INVENTION

Problems to be Solved by the Invention

Also, in the gas sensor of Patent Document 1, a through-hole (inner gas discharge hole) is formed in the side wall of a forward end portion of the inner protector so as to discharge the gas-to-be-detected from the inside of the inner protector to the outside thereof. Moreover, a through-hole (outer gas discharge hole) is formed in a bottom portion of a forward end portion of the outer protector which surrounds the forward end portion of the inner protector in order to discharge the gas-to-be-detected from the inside of the outer protector to the outside thereof. Notably, the outer gas discharge hole is formed on the center axis of the outer protector. Also, the forward end portion of the outer protector has a cylindrical side wall and a disk-like bottom portion.

In the gas sensor of Patent Document 1 configured as described above, the gas-to-be-detected taken into the interior of the gas sensor is discharged to the outside thereof through the following route. Specifically, the gas-to-be-detected introduced into the internal space of the inner protector is discharged from the internal space to a side (radially outer side) through the inner gas discharge hole, flows through the space between the side wall of the forward end portion of the outer protector and the side wall of the forward end portion of the inner protector. Subsequently, the gas-to-be-detected flows through the space toward the axially forward end side, and then flows through the gap between the bottom portion of the outer protector and the bottom portion of the inner protector toward the center axis. The gas-to-be-detected is then discharged to the outside of the protector through the outer gas discharge hole formed in the bottom portion of the outer protector.

However, when the above-mentioned gas discharge passage is employed, the gas-to-be-detected introduced into the internal space of the inner protector cannot be discharged to the outside efficiently and quickly, whereby the responsiveness of the gas sensor may deteriorate.

The present invention was made in view of the present situation, and an object of the invention is to provide a gas sensor having a protector which is improved in gas discharge performance to thereby enhance the responsiveness of the gas sensor and which can properly protect a detection element from adhesion of water.

Means for Solving the Problems

One mode of the present invention is a gas sensor comprising a detection element extending in an axial direction and having a detection portion which is provided on a forward end side thereof and adapted to detect a particular gas component contained in a gas-to-be-detected; a housing which surrounds a radial circumference of the detection element in a state in which the detection portion projects from a forward end of the housing; and a protector which is fixed to the housing and which surrounds the circumference of the detection portion, the protector including an inner protector which accommodates the detection portion in an internal space of the inner protector, and an outer protector which accommodates the inner protector, wherein the inner protector includes a tubular first inner wall having a first inner hole extending therethrough, a tubular second inner wall which is located on an axially forward end side of the first inner wall and which has a diameter smaller than that of the first inner wall, the second inner wall having a second inner hole extending therethrough, and an inner bottom wall which closes a forward end of the second inner wall; and the outer protector includes a tubular first outer wall which surrounds the circumference of the first inner wall and forms a tubular first space between the first outer wall and the first inner wall, the first outer wall having a first outer hole extending therethrough at a position on the axially forward end side in relation to the first inner hole, a tubular second outer wall which is located on the axially forward end side of the first outer wall, which has a diameter smaller than that of the first outer wall and larger than that of the first inner wall, and which surrounds the circumference of the second inner wall and forms a tubular second space between the second outer wall and the second inner wall, the second outer wall being airtightly connected, at a base end portion thereof, to a forward end portion of the first inner wall, and extending toward the axially forward end side in relation to the inner bottom wall, and a taper wall which is located on the axially forward end side of the second outer wall, which has the shape of a tapered tube whose diameter decreases toward the axially forward end side, and which has a second outer hole which is a forward end opening of the taper wall, the entirety of the taper wall being disposed on the axially forward end side in relation to the inner bottom wall.

In the above-described gas sensor, the gas-to-be-detected flows through the interior of the protector along the following route. Specifically, the gas-to-be-detected is introduced into the first space (the space between the first outer wall and the first inner wall) from the outside through the first outer hole of the outer protector (outer gas introduction hole). The gas-to-be-detected then flows within the first space toward the axially base end side, and is introduced into the internal space of the inner protector through the first inner hole of the inner protector (inner gas introduction hole). After that, the gas-to-be-detected flows within the internal space toward the axially forward end side, is discharged to the outside of the inner protector through the second inner hole of the inner protector (inner gas discharge hole), and is introduced into the second space (the space between the second outer wall and the second inner wall). After being introduced into an in-taper space surrounded by the taper wall of the outer protector, the gas-to-be-detected is discharged to the outside of the protector through the second outer hole of the outer protector (outer gas discharge hole).

Notably, the first inner hole of the inner protector is located on the axially base end side in relation to the detection portion of the detection element, and the second inner hole is located on the axially forward end side in relation to the detection portion of the detection element. Therefore, a portion of the gas-to-be-detected introduced into the internal space through the first inner hole is led to the detection portion of the detection element in the course of flowing within the internal space toward the axially forward end side and being discharged to the outside of the inner protector through the second inner hole.

Incidentally, in the case where the base end portion of the second outer wall of the outer protector is not connected to the forward end portion of the first inner wall of the inner protector in an airtight manner (in a state in which gas cannot flow through the connected portion), a portion of the gas-to-be-detected introduced into the first space from the outside through the first outer hole flows into the second space through the gap between the second outer wall and the first inner wall, and then flows (or tries to flow) into the internal space of the inner protector through the second inner hole. Therefore, the gas introduced into the internal space of the inner protector through the first inner hole is prevented from being discharged to the outside of the inner protector through the second inner hole. As a result, the gas discharge performance may deteriorate.

In contrast, in the above-described gas sensor, the base end portion (portion opposite the forward end portion) of the second outer wall of the outer protector is connected to the forward end portion of the first inner wall of the inner protector over the entire circumference around the axis in an airtight manner (in a state in which gas cannot flow through the connected portion).

Therefore, the gas-to-be-detected introduced into the first space from the outside through the first outer hole does not flow from the first space directly to the second space, and assuredly flows within the first space toward the axially base end side, and is introduced through the first inner hole into the internal space of the inner protector (space which accommodates the detection portion of the detection element). As a result, the gas-to-be-detected introduced into the internal space of the inner protector through the first inner hole can be smoothly discharged to the outside of the inner protector through the second inner hole.

Notably, the base end portion of the second outer wall and the forward end portion of the first inner wall may be connected together by crimping, fitting, or welding.

Moreover, in the above-described gas sensor, the outer protector has a tapered-tubular (truncated conical tubular) taper wall which is located on the axially forward end side of the second outer wall and whose diameter decreases toward the axially forward end side. This taper wall has the second outer hole, which is a forward end opening (which opens at the forward end).

By virtue of the above-described configuration, in a region outside the protector (within a flow passage of the gas-to-be-detected), the flow velocity of the gas-to-be-detected increases in the vicinity of the forward end of the taper wall (in the vicinity of the second outer hole), and due to the Venturi effect, a strong negative pressure is produced in the vicinity of the forward end of the taper wall (in the vicinity of the second outer hole). As a result, the gas-to-be-detected introduced into the internal space is effectively and quickly discharged to the outside of the protector while being drawn toward the second outer hole located at the forward end of the taper wall.

In addition, the gas-to-be-detected introduced into the taper space flows toward the forward end side along the taper wall whose diameter decreases toward the axially forward end side, and flows to the outside through the second outer hole, which is the forward end opening of the taper wall, while maintaining the flow direction. Through employment of the configuration for forcing the gas-to-be-detected to flow straight toward the second outer hole and discharging it, the gas-to-be-detected can be discharged efficiently and smoothly.

Moreover, in the above-described gas sensor, the entirety of the taper wall is disposed on the axially forward end side in relation to the inner bottom wall of the inner protector. Therefore, the gas-to-be-detected discharged from the second inner hole of the second inner wall of the inner protector passes through the second space between the second outer wall and the second inner wall, enters the large in-taper space surrounded by the taper wall only (where the inner protector does not exist), and then flows toward the second outer hole.

Incidentally, in the case where, unlike the above-described gas sensor, the taper wall is disposed such that a portion (located on the base end side) of the taper wall is located on the axially base end side in relation to the inner bottom wall of the inner protector, the gas-to-be-detected discharged from the second inner hole passes through the gap between the taper wall and the second inner wall. Since the taper wall has the shape of a tapered tube whose diameter decreases toward the axially forward end side, the space between the taper wall and the second inner wall becomes smaller than the second space between the second outer wall and the second inner wall. Therefore, in this case, the gas flow passage becomes narrower, and the gas discharge performance deteriorates.

In contrast, in the above-described gas sensor, the entire taper wall is located on the axially forward end side in relation to the inner bottom wall of the inner protector. Therefore, a large gas flow passage can be secured, whereby the gas discharge performance becomes good.

Accordingly, the above-described gas sensor has an improved gas discharge performance, and thus has an enhanced responsiveness.

Also, the above-described gas sensor has an inner bottom wall which closes the forward end of the second inner wall. Namely, the inner bottom wall of the inner protector does not have a through-hole which penetrates the inner bottom wall. As a result, the forward end opening (the second outer hole) of the taper wall and the inner bottom wall of the inner protector overlap each other as viewed in the axial direction. Therefore, even when water enters from the outside to the interior of the protector through the second outer hole, which is the forward end opening of the taper wall, the inner bottom wall of the inner protector prevents the water from flowing directly into the interior of the inner protector. As a result, it is possible to properly protect the detection element accommodated within the inner protector from adhesion of water.

In the above-described gas sensor, preferably, a relation $L1<L2<L3$ is satisfied, where $L1$ represents the shortest distance between the second outer wall and the second inner wall at a forward end of the second inner hole (a portion of the second inner wall located at a position corresponding to the forward ends of the second inner hole), $L2$ represents the shortest distance between a base end of the taper wall and the inner protector, and $L3$ represents the shortest distance between a forward end of the taper wall and the inner bottom wall.

In the above-described gas sensor, the relation $L1<L2<L3$ is satisfied. As a result, the gas flow passage tends to expand from the second inner hole of the inner protector toward the second outer hole of the outer protector. Therefore, the above-described gas sensor has a further improved gas discharge performance.

Incidentally, when water from the outside enters the interior of the outer protector through the second outer hole of the outer protector, the water may flow from the second outer hole of the outer protector toward the second inner hole of the inner protector. However, since the above-described gas sensor satisfies the above-mentioned relation $L1<L2<L3$, the flow passage of the water tends to narrow from the second outer hole of the outer protector toward the second inner hole of the inner protector. As a result, even when water from the outside enters the interior of the outer protector through the second outer hole of the outer protector, the water hardly flows into the second space, and hardly flows into the interior of the inner protector through the second inner hole. Therefore, the water becomes unlikely to adhere to the detection element accommodated within the inner protector.

In any of the above-described gas sensors, preferably, a base end portion of the first outer wall is located on a radially outer side of a forward end portion of the housing; and the first outer wall has a tubular shape and extends straight from a position located on the radially outer side of the forward end portion of the housing toward the axially forward end side.

In the gas sensor of the above-described Patent Document 1 (Japanese Patent Application Laid-Open No. 2011-112557), a large diameter portion of the outer protector is located on the radially outer side of the forward end portion of the housing (metallic shell). Further, a trunk portion which is smaller in diameter than the large diameter portion is disposed on the radially inner side in relation to the large diameter portion with a step portion which is bent radially inward being disposed therebetween. The trunk portion forms a space in cooperation with a trunk portion (corresponding to the first inner wall of the present invention) of the inner protector.

Meanwhile, in the above-described gas sensor, the base end portion of the first outer wall is located on the radially outer side of the forward end portion of the housing, and the first outer wall has the shape of a tube which extends straight from a position located on the radially outer side of the forward end portion of the housing toward the axially forward end side. As described above, in the above-described gas sensor, unlike the gas sensor of Patent Document 1, the first outer wall extends straight from the position located on the radially outer side of the forward end portion of the housing toward the axially forward end side without being bent toward the radially inner side. As a result, as compared with the case where the first outer wall is bent toward the radially inner side, a larger gap can be formed between the first outer wall and the first inner wall. Therefore, water entering the interior of the outer protector through the first outer hole can be stored in the gap in a large amount, and can be discharged through the first outer hole. As a result, even when water enters through the first outer hole, the water hardly reaches the first inner hole and hardly flows into the interior of the inner protector through the first inner hole. Accordingly, in the above-described gas sensor, water hardly adheres to the detection element.

In any of the above-described gas sensors, preferably, the diameter of an inscribed circle of the first inner hole is smaller than that of the first outer hole.

The diameter of a circle (or a sphere) inscribed to the first inner hole (a wall surface which forms the first inner hole) corresponds to the maximum diameter of water droplets which can pass through the first inner hole. Similarly, the diameter of a circle (or a sphere) inscribed to the first outer hole (a wall surface which forms the first outer hole) corresponds to the maximum diameter of water droplets which can pass through the first outer hole. Accordingly, by making the diameter of the inscribed circle (inscribed sphere) of the first inner hole smaller than the diameter of the inscribed circle (inscribed sphere) of the first outer hole, it becomes more difficult for water to pass through the first inner hole, as compared with the first outer hole. As a result, even when water has entered the interior of the outer protector through the first outer hole, the water is less likely to flow into the interior of the inner protector through the first inner hole. Accordingly, in the above-described gas sensor, water is less likely to adhere to the detection element.

In any of the above-described gas sensors, preferably, a relation $A<B<C$ is satisfied, where A represents the total opening area of the second outer hole, B represents the total opening area of the second inner hole, and C represents the total opening area of the first inner hole.

In the above-described gas sensor, as described above, the gas-to-be-detected introduced into the internal space of the inner protector through the first inner hole of the inner protector flows within the internal space toward the axially forward end side, and is discharged to the outside of the inner protector through the second inner hole of the inner protector. The gas-to-be-detected is then discharged to the outside of the protector through the second outer hole of the outer protector. Incidentally, the smaller the opening area of a hole, the greater the difficulty for the gas to pass through the hole. Accordingly, of the second outer hole, the second inner hole, and the first inner hole, a hole which has the smallest opening area (total opening area) determines the amount of the gas discharged to the outside of the protector (discharge performance).

In contrast, the above-described gas sensor, the total opening area A of the second outer hole, the total opening area B of the second inner hole, and the total opening area C of the first inner hole satisfy the relation A<B<C. Namely, of the totals opening areas of the second outer hole, the second inner hole, and the first inner hole, the total opening area A of the second outer hole is made smallest. Accordingly, in the above-described gas sensor, the amount of gas discharged to the outside of the protector (discharge performance) is adjusted by the second outer hole without being affected by the gas discharge performance of the second inner hole and that of the first inner hole.

In addition, of the totals areas of the second outer hole, the second inner hole, and the first inner hole, the total opening area C of the first inner hole is made largest. Therefore, the introduction of the gas into the internal space of the inner protector through the first inner hole becomes easier. As a result, the responsiveness of the gas sensor can be enhanced.

Notably, in the case where a plurality of second outer holes are formed, the "total opening area" of the second outer hole is the sum of the opening areas of the second outer holes. This also applies to the second inner hole and the first inner hole. The number of the second outer holes, the number of the first inner holes, and the number of the second inner holes, or the opening area per hole of the second outer holes, that of the first inner holes, and that of the second inner holes may be properly set so as to satisfy the above-described relation among their total opening areas.

In the above-described gas sensor, preferably, a relation C<D is satisfied, where C represents the total opening area of the first inner hole, and D represents the total opening area of the first outer hole.

As described above, in the above-described gas sensor, the gas is introduced into the interior of the protector from the outside through the first outer hole of the outer protector, and the introduced gas then passes through the first inner hole of the inner protector and the second inner hole of the inner protector and is discharged to the outside through the second outer hole of the outer protector.

Furthermore, in the above-described gas sensor, the total opening area D of the first outer hole and the total opening area C of the first inner hole satisfies the relation C<D. Also, as described above, the total opening area A of the second outer hole, the total opening area B of the second inner hole, and the total opening area C of the first inner hole satisfy the relation A<B<C<D. Accordingly, in the above-described gas sensor, the total opening area A of the second outer hole, the total opening area B of the second inner hole, the total opening area C of the first inner hole, and the total opening area D of the first outer hole satisfy the relation A<B<C<D. As described above, of the totals areas of the first outer hole, the first inner hole, the second inner hole, and the second outer hole, the total opening area of the first outer hole is made largest. Therefore, the introduction of the gas into the interior of the protector through the first outer hole becomes easier. As a result, the responsiveness of the gas sensor can be enhanced.

Notably, in the case where a plurality of first outer holes are formed, the "total opening area" of the first outer hole is the sum of the opening areas of the first outer holes. The number of the first outer holes and the number of the first inner holes, or the opening area per hole of the first outer holes and that of the first inner holes may be properly set so as to satisfy the above-described relation between their total opening areas.

In any of the above-described gas sensors, preferably, the inner protector has a connection wall for connecting the first inner wall and the second inner wall together; and the connection wall has the shape of a tapered tube whose diameter decreases toward the axially forward end side.

Since the connection wall, which connects the first inner wall and the second inner wall, has the shape of a tapered tube (truncated conical tube) whose diameter decreases toward the axially forward end side, as compared with the case where the connection wall has the shape of a flat ring extending orthogonally to the axis, the flow of the gas-to-be-detected which flows within the internal space toward the axially forward end side (from the space surrounded by the first inner wall to the space surrounded by the second inner wall) can be made smooth. Accordingly, the gas sensor has a further enhanced gas discharge performance.

In any of the above-described gas sensors, preferably, the first outer hole is located at a forward end portion of the first outer wall; and the first inner hole is located at a base end portion of the first inner wall.

By disposing the first outer hole and the first inner hole at the above-described positions, the first inner hole can be greatly separated from the first outer hole toward the axially base end side. Therefore, even when water enters through the first outer hole, the water becomes less likely to reach the first inner hole, and becomes less likely to flow into the interior of the inner protector through the first inner hole. Therefore, in the above-described gas sensor, water becomes more unlikely to adhere to the detection element.

MODES FOR CARRYING OUT THE INVENTION

Embodiment

An embodiment of the present invention will next be described with reference to the drawings.

Figure 1:
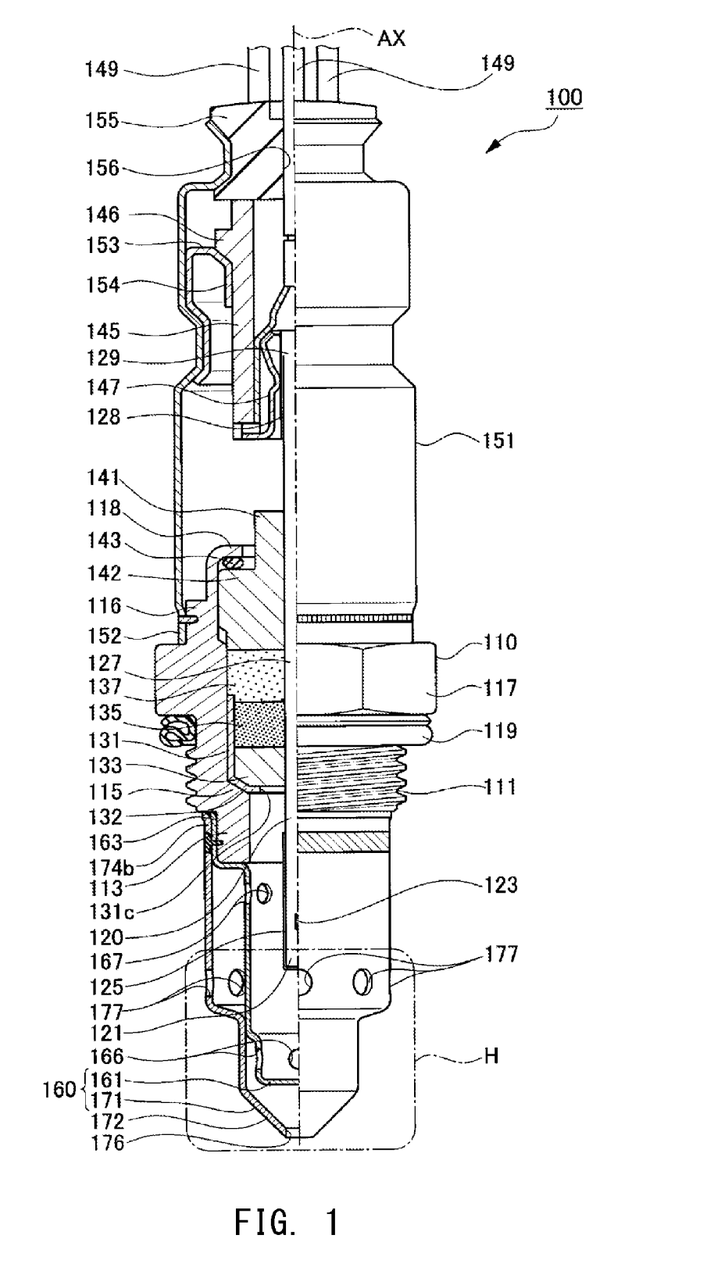
FIG. 1 Half sectional view of a gas sensor according to an embodiment.
Figure 2:
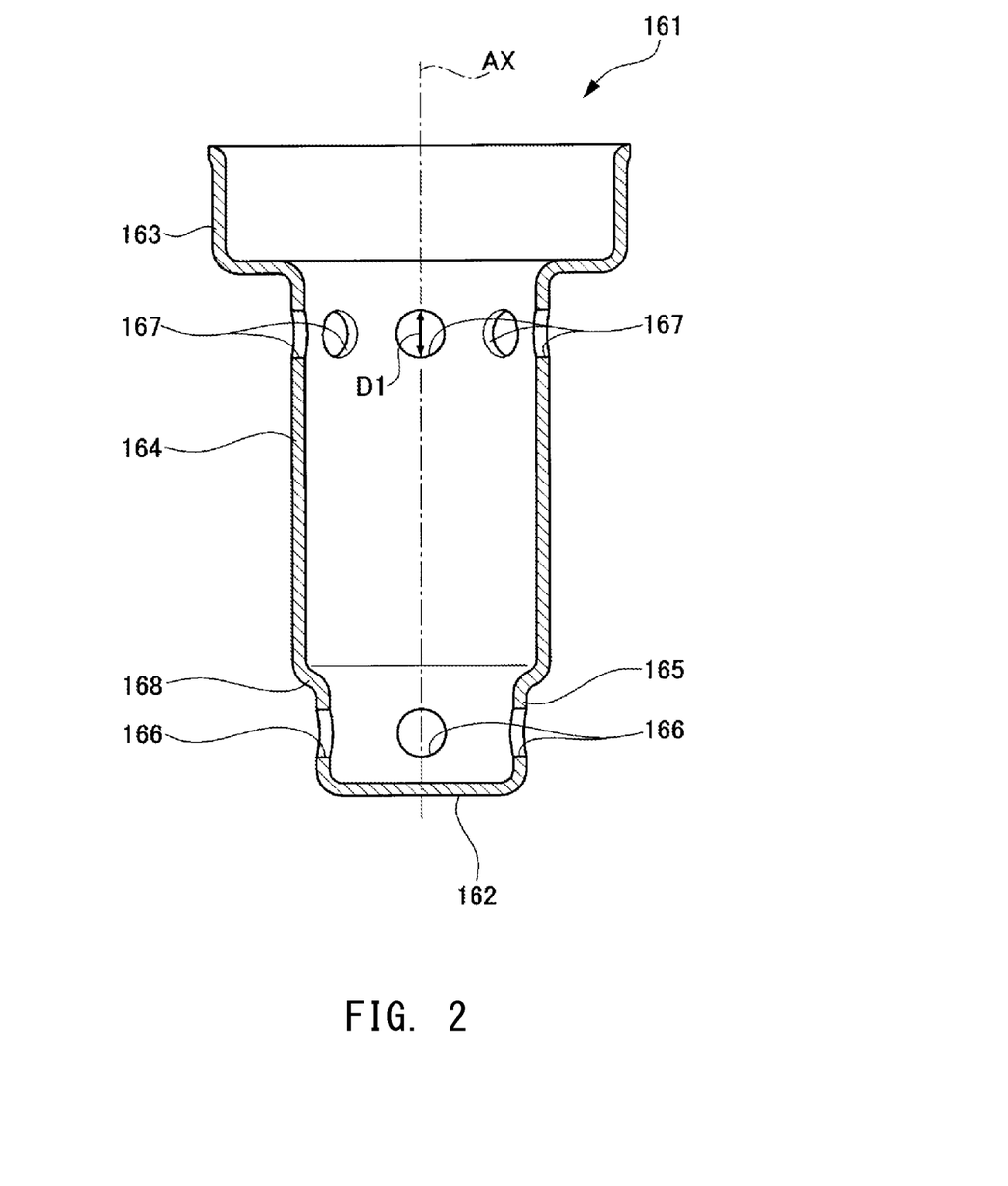
FIG. 2 Sectional view of an inner protector of the gas sensor.
Figure 3:
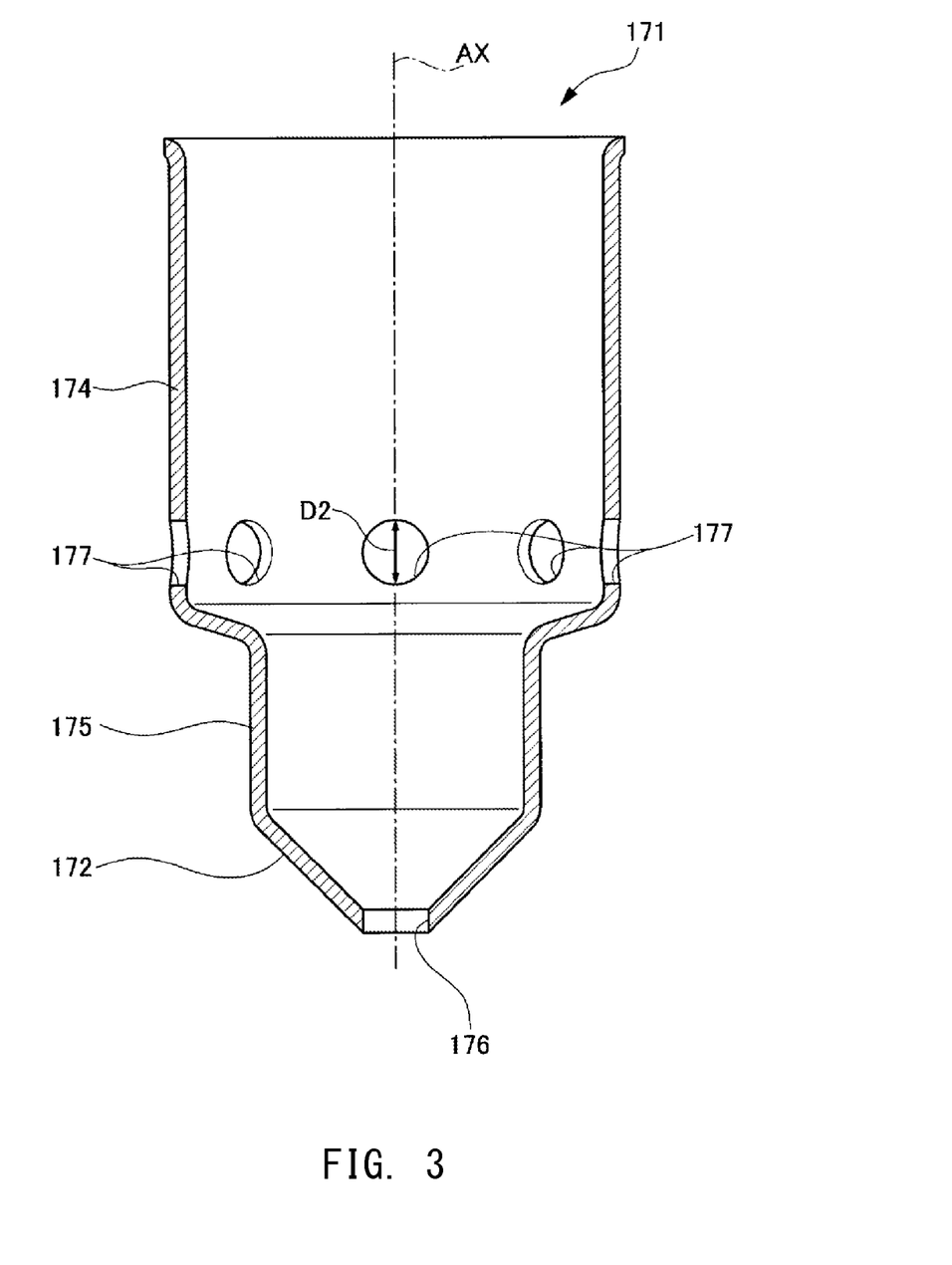
FIG. 3 Sectional view of an outer protector of the gas sensor.
Figure 4:
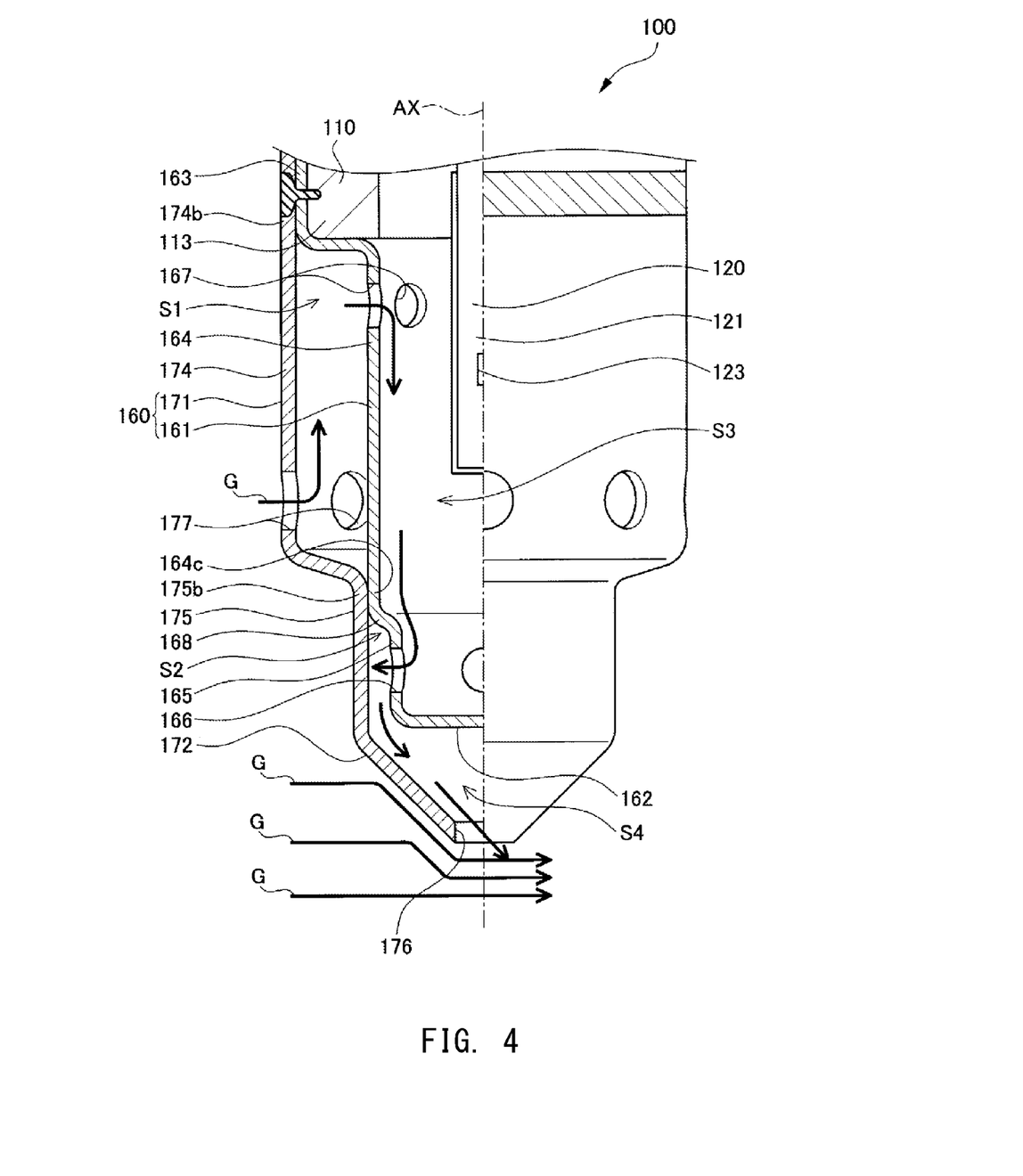
FIG. 4 View used for describing a flow of a gas-to-be-detected within the gas sensor.

FIG. 1 is a half sectional view of a gas sensor 100 of the present embodiment. FIG. 2 is a sectional view of an inner protector 161 of the gas sensor 100. FIG. 3 is a sectional view of an outer protector 171 of the gas sensor 100. FIG. 4 is an enlarged view of a forward end portion of the gas sensor 100 which is attached to an exhaust pipe of an unillustrated automobile such that the forward end portion of the gas sensor 100 is located within the exhaust pipe. FIG. 4 is used for describing the flow of exhaust gas (gas-to-be-detected) G.

Notably, in FIGS. 1 to 4, the lower side is an axially forward end side (hereinafter also referred to as the forward end side for simplicity), and the upper side is an axially base end side (hereinafter also referred to as the base end side for simplicity). Also, in FIG. 4, the left side is the upstream side (engine side) of the exhaust pipe through which exhaust gas G flows, and the right side is the downstream side of the exhaust pipe.

The gas sensor 100 is a so-called full range air/fuel ratio sensor which is attached to the exhaust pipe of an unillustrated automobile and which holds therein a detection element 120. A detection portion 121 of the detection element 120 is exposed to exhaust gas (gas-to-be-detected) which flows through the exhaust pipe so as to detect the air/fuel ratio of the exhaust gas from the concentration of oxygen (particular gas component) contained in the exhaust gas.

As shown in FIG. 1, this gas sensor 100 is mainly composed of a tubular metallic shell (housing) 110 extending in an axial direction (the direction along an axis AX, the vertical direction in FIG. 1); the plate-shaped detection element 120 held inside the metallic shell 110; an outer cylinder 151 fixedly provided on the base end side of the metallic shell 110; and a double-wall protector 160 which is fixedly provided on the forward end side of the metallic shell 110 and which is composed of an inner protector 161 and an outer protector 171.

The detection element 120 has a plate-like shape (strip-like shape) extending in the axial direction, and a forward end portion of the detection element 120 is the detection portion 121 for detecting the oxygen gas component contained in the exhaust gas. This detection element 120 has a known structure and is formed by bonding together for unification a plate-shaped gas detecting body for detecting oxygen concentration and a plate-shaped heater body for heating the gas detecting body for quick activation thereof. The gas detecting body is composed of a solid electrolyte body which predominantly contains zirconia, and a pair of electrodes (detection and reference electrodes) which predominantly contains platinum. The pair of electrodes are disposed on the detection portion 121.

The detection portion 121 has a gas introduction portion 123 for introducing the exhaust gas into the interior of the element. This gas introduction portion 123 is formed of a porous material and has a rectangular shape in a planar view. In order to protect the detection electrode from poisoning by the exhaust gas, a protection layer 125 is provided on the detection portion 121 such that the protection layer 125 covers the outer surface of the detection portion 121. Also, five electrode pads 128 (one of which is shown in FIG. 1) for allowing external connection with the electrodes of the gas detecting body and the heater body are formed on a base end portion 129 of the detection element 120.

A bottomed tubular metal cup 131 is disposed at a position slightly deviated forward from the center of a trunk portion 127 of the detection element 120 in such a manner that the detection element 120 is inserted through the interior of the metal cup 131 with the detection portion 121 projecting from an opening 131c formed in the bottom of the metal cup 131. The metal cup 131 is a member for holding the detection element 120 in the metallic shell 110. A forward-end peripheral edge portion 132 of the metal cup 131 is tapered such that the diameter of the metal cup 131 decreases toward the forward end thereof.

The metal cup 131 contains a ceramic ring 133 made of alumina and a first talc ring 135 formed by compacting a talc powder, in such a manner that the detection element 120 is inserted through the ceramic ring 131 and through the first talc ring 135. The first talc ring 135 is crushed within the metal cup 131 so as to tightly fill an associated space, thereby holding the detection element 120 in position in the metal cup 131.

The detection element 120 united with the metal cup 131 is held by the tubular metallic shell 110 such that its radial circumference is surrounded by the metallic shell 110. The metallic shell 110 is adapted to fixedly attach the gas sensor 100 to the exhaust pipe of the automobile. The metallic shell 110 is formed from low-carbon steel such as SUS430. An external thread portion 111 for attachment to the exhaust pipe is formed on the forward end side of the outer circumference of the metallic shell 110. The metallic shell 110 has an annular forward end fixing portion 113 which is projectingly formed on the forward end side of the external thread portion 111 and to which the protector 160 to be described later is fixed.

The metallic shell 110 also has a tool engagement portion 117 which is formed at the center of the outer circumference of the metallic shell 110 and with which a mounting tool is engaged. In order to prevent leakage of gas when the gas sensor 100 is attached to the exhaust pipe, a gasket 119 is fitted to a portion of the metallic shell 110 between the tool engagement portion 117 and the external thread portion 111. The metallic shell 110 further has a base end fixing portion 116 which is formed on the base end side of the tool engagement portion 117 and to which the outer cylinder 151 to be described later is fixed. The metallic shell 110 further has a crimp portion 118 which is formed on the base end side of the base end fixing portion 116 and which is adapted to crimp-hold the detection element 120 in the metallic shell 110.

The metallic shell 110 has a stepped portion 115 which is formed on the forward end side of the inner circumference of the metallic shell 110 and which is tapered such that its diameter decreases toward the forward end side. The tapered front-end peripheral edge portion 132 of the metal cup 131 which holds the detection element 120 is engaged with the stepped portion 115.

Furthermore, a second talc ring 137 is disposed in the metallic shell 110 to be located on the base end side of the metal cup 131 in such a state that the detection element 120 is inserted through the second talc ring 137. A tubular sleeve 141 is fitted into the metallic shell 110 in such a manner as to press the second talc ring 137 from the base end side of the second talc ring 137. The sleeve 141 has a step-like shoulder portion 142. An annular crimp packing 143 is disposed on the shoulder portion 142. The crimp portion 118 of the metallic shell 110 is crimped in such a manner as to press the shoulder portion 142 of the sleeve 141 toward the forward end side via the crimp packing 143.

Being pressed by the sleeve 141, the second talc ring 137 is crushed within the metallic shell 110, thereby tightly filling an associated space. By means of the second talc ring 137 and the first talc ring 135, which is previously placed in the metal cup 131, the metal cup 131 and the detection element 120 are held in position in the metallic shell 110. The crimp packing 143 disposed between the crimp portion 118 and the shoulder portion 142 of the sleeve 141 maintains the airtightness of the interior of the metallic shell 110, to thereby prevent leakage of combustion gas.

A base end portion 129 of the detection element 120 projects toward the base end side beyond the crimp portion 118, which is the base end portion of the metallic shell 110. The base end portion 129 is covered with a tubular separator 145 formed from an electrically insulative ceramic. The separator 145 internally holds five connection terminals 147 (one of which is shown in FIG. 1) electrically connected to the five electrode pads 128 formed on the base end portion 129 of the detection element 120. Also, the separator 145 accommodates connection portions between the connection terminals 147 and corresponding five lead wires 149 (three of which are shown in FIG. 1), which extend to the exterior of the gas sensor 100, while insulating them from one another.

The tubular outer cylinder 151 is disposed in such a manner as to surround the circumference of the separator 145. The outer cylinder 151 is made of stainless steel (SUS304 in the present embodiment). A forward end opening portion 152 of the outer cylinder 151 is disposed on the radially outer side of the base end fixing portion 116 of the metallic shell 110. The forward end opening portion 152 is crimped radially inward, and laser welding is performed on the forward end opening portion 152 along the entire outer circumference thereof, whereby the forward end opening portion 152 is connected to the base end fixing portion 116.

A tubular metal holder 153 is disposed in the gap between the outer cylinder 151 and the separator 145. The metal holder 153 has a support portion 154, which is formed by inwardly bending a base end of the metal holder 153. The separator 145 is inserted through the metal holder 153 such that a flange portion 146 formed on the outer circumference of a base end portion of the separator 145 is engaged with the support portion 154, whereby the separator 145 is supported by the support portion 154. In this condition, a portion of the outer cylinder 151 where the metal holder 153 is disposed is crimped radially inward, whereby the metal holder 153 which supports the separator 145 is fixed to the outer cylinder 151.

A grommet 155 made of fluorine-containing rubber is fitted into a base end opening of the outer cylinder 151. The grommet 155 has five insertion holes 156 (one of which is shown in FIG. 1). The five lead wires 149 extending outwardly from the separator 145 are airtightly inserted through the respective insertion holes 156. In this condition, while the grommet 155 presses the separator 145 toward the forward end side, a portion of the outer cylinder 151 which corresponds to the grommet 155 is crimped radially inward, whereby the grommet 155 is fixed to the outer cylinder 151.

The detection portion 121 of the detection element 120 held by the metallic shell 110 projects from the forward end fixing portion 113, which is a forward end portion of the metallic shell 110. The protector 160 is fitted to the forward end fixing portion 113 so as to protect the detection portion 121 of the detection element 110 from fouling with deposits (poisoning substances, such as fuel ash and oil) contained in exhaust gas and from breakage caused by adhesion of water. The protector 160 is fixed to the forward end fixing portion 113 by laser welding. This protector 160 includes a tubular inner protector 161 having a bottom, and an outer protector 171 which accommodates the inner protector 161 (see FIGS. 1 to 4).

As shown in FIG. 4, the inner protector 161 is fixed to the metallic shell 110 in a state in which the detection portion 121 of the detection element 120 is disposed in the internal space S3 of the inner protector 161. As shown in FIGS. 1, 2, and 4, the inner protector 161 has a base end portion 163; a first inner wall 164 located on the axially forward end side (the lower side in FIGS. 1, 2, and 4) of the base end portion 163; a second inner wall 165 located on the axially forward end side of the first inner wall 164, and a disk-like inner bottom wall 162 which closes the forward end of the second inner wall 165.

The first inner wall 164 has a cylindrical tubular shape and has first inner holes 167 which penetrate the first inner wall 164. Notably, in the present embodiment, eight first inner holes 167 having the same shape (same dimension) are formed at equal intervals in the circumferential direction. All the eight first inner holes 167 are located on the axially base end side (the upper side in FIGS. 1 and 4) in relation to the detection portion 121 of the detection element 120.

The second inner wall 165 has a cylindrical tubular shape, is smaller in diameter than the first inner wall 164, and has second inner holes 166 which penetrate the second inner wall 165. Notably, in the present embodiment, four second inner holes 166 are formed at equal intervals in the circumferential direction. All the four second inner holes 166 are located on the axially forward end side (the lower side in FIGS. 1 and 4) in relation to the detection portion 121 of the detection element 120.

Notably, although the inner diameters of the first inner wall 164 and the second inner wall 165 are smaller than the outer diameter of the forward end fixing portion 113 of the metallic shell 110, the base end portion 163 has an increased diameter such that the base end portion 163 is located on the outer side of the forward end fixing portion 113.

The outer protector 171 is fixed to the metallic shell 110 in a state in which the outer protector 171 accommodates the inner protector 161 therein. The outer protector 171 has a first outer wall 174; a second outer wall 175 located on the axially forward end side of the first outer wall 174, and a taper wall 172 located on the axially forward end side of the second outer wall 175 (see FIGS. 1, 3, and 4).

The first outer wall 174 has a cylindrical tubular shape, and surrounds the circumference of the first inner wall 164 while forming a tubular first space S1 in cooperation with the first inner wall 164 of the inner protector 161. Further, the first outer wall 174 has first outer holes 177 which penetrate the first outer wall 174 and are located on the axially forward end side in relation to the first inner holes 167 of the inner protector 161 (see FIGS. 1 and 4). Notably, in the present embodiment, eight first outer holes 177 having the same shape (same dimension) are formed at equal intervals in the circumferential direction. All the eight first outer holes 177 are located on the axially forward end side in relation to the first inner holes 167 of the inner protector 161.

The second outer wall 175 has a cylindrical tubular shape, and has an inner diameter smaller than the inner diameter of the first outer wall 174 and larger than the outer diameter of the first inner wall 164. Further, the second outer wall 175 surrounds the circumference of the second inner wall 165 while forming a tubular second space S2 in cooperation with the second inner wall 165. The second outer wall 175 extends to a point on the axially forward end side of the inner bottom wall 162 of the inner protector 161.

In particular, in the present embodiment, the second outer wall 175 is connected at its base end portion 175b to a forward end portion 164c of the first inner wall 164 in an airtight manner (in a state in which gas cannot flows through the connected portion). Specifically, the base end portion 175b of the second outer wall 175 and the forward end portion 164c of the first inner wall 164 are airtightly connected (fitted) together over the entire circumference around the axis AX by means of press-fitting the forward end portion 164c of the first inner wall 164 into the base end portion 175b of the second outer wall 175.

The taper wall 172 has the shape of a tapered tube (truncated conical tube) whose diameter decreases toward the axially forward end side. This taper wall 172 has a second outer hole 176, which is a forward end opening of the outer protector 171. In particular, in the present embodiment, the entirety of the taper wall 172 is disposed on the axially forward end side in relation to the inner bottom wall 162 of the inner protector 161.

The base end portion 174b of the first outer wall 174 of the outer protector 171 is disposed on the outer side of the base end portion 163 of the inner protector 161. Laser welding is performed along the entire outer circumference of the base end portion 174b of the outer protector 171 so as to fix (weld) the base end portion 174b of the outer protector 171, together with the base end portion 163 of the inner protector 161, to the forward end fixing portion 113 of the metallic shell 110.

In the gas sensor 100 of the present embodiment, the exhaust gas (gas-to-be-detected) G within the exhaust pipe flows through the interior of the protector 160 (the inner protector 161 and the outer protector 171) along the following route.

Specifically, as shown in FIG. 4, the exhaust gas G having flowed through the exhaust pipe from the upstream side thereof (the left side in FIG. 4) toward the gas sensor 100 is introduced into the first space S1 within the protector 160 (the space between the first outer wall 174 and the first inner wall 164) through the first outer holes 177 of the outer protector 171 (outer gas introduction holes).

The exhaust gas G then flows within the first space S1 toward the axially base end side (the upper side in FIG. 4), and is introduced into the internal space S3 of the inner protector 161 through the first inner holes 167 of the inner protector 161 (inner gas introduction holes). After that, the exhaust gas G flows within the internal space S3 toward the axially forward end side (the lower side in FIG. 4), is discharged to the outside of the inner protector 161 through the second inner holes 166 of the inner protector 161 (inner gas discharge holes), and is introduced into the second space S2 (the space between the second outer wall 175 and the second inner wall 165). After being introduced into an in-taper space S4 surrounded by the taper wall 172 of the outer protector 171, the exhaust gas G is discharged to the outside of the protector 160 through the second outer hole 176 of the outer protector 171 (outer gas discharge hole).

Notably, the first inner holes 167 of the inner protector 161 are located on the axially base end side in relation to the detection portion 121 of the detection element 120, and the second inner holes 166 are located on the axially forward end side in relation to the detection portion 121. Therefore, a portion of the exhaust gas G introduced into the internal space S3 through the first inner holes 167 is led to the gas introduction portion 123 of the detection portion 121 in the course of flowing within the internal space S3 toward the axially forward end side and being discharged to the outside of the inner protector 161 through the second inner holes 166.

Incidentally, in the case where the base end portion of the second outer wall of the outer protector is not connected to the forward end portion of the first inner wall of the inner protector in an airtight manner (in a state in which gas cannot flow through the connected portion), a portion of the exhaust gas introduced into the first space from the outside through the first outer holes flows into the second space through the gap between the second outer wall and the first inner wall, and then flows (or tries to flow) into the internal space of the inner protector through the second inner holes. Therefore, the gas introduced into the internal space of the inner protector through the first inner holes is prevented from being discharged to the outside of the inner protector through the second inner holes. As a result, the gas discharge performance may deteriorate.

In contrast, in the gas sensor 100 of the present embodiment, the base end portion 175b of the second outer wall 175 of the outer protector 171 is connected to (fitted onto) the forward end portion 164c of the first inner wall 164 of the inner protector 161 over the entire circumference around the axis in an airtight manner (in a state in which gas cannot flow through the connected portion).

Therefore, the exhaust gas G introduced into the first space S1 from the outside through the first outer holes 177 does not flow from the first space S1 directly to the second space S2, and assuredly flows within the first space S1 toward the axially base end side, and is introduced into the internal space S3 of the inner protector 161 (space which accommodates the detection portion 120 of the detection element 120) through the first inner holes 167 (see FIG. 4). As a result, the exhaust gas G introduced into the internal space S3 of the inner protector 161 through the first inner holes 167 can be smoothly discharged to the outside of the inner protector 161 through the second inner holes 166.

Moreover, in the gas sensor 100 of the present embodiment, the outer protector 171 has, at its axially forward end portion, the tapered-tubular (truncated conical tubular) taper wall 172 whose diameter decreases toward the axially forward end side. The taper wall 172 has the second outer hole 176, which is a forward end opening.

By virtue of the above-described configuration, as indicated by arrows in FIG. 4, in a region outside the protector 160 (within the exhaust pipe), the flow velocity of the exhaust gas G increases in the vicinity of the forward end of the taper wall 172 (in the vicinity of the second outer hole 176), and due to the Venturi effect, a strong negative pressure can be produced in the vicinity of the forward end of the taper wall 172 (in the vicinity of the second outer hole 176). As a result, the exhaust gas G introduced into the internal space S3 is effectively and quickly discharged to the outside of the protector 160 while being drawn toward the second outer hole 176 located at the forward end of the taper wall 172.

In addition, as indicated by arrows in FIG. 4, the exhaust gas G introduced into the taper space S4 flows toward the forward end side along the taper wall 172 whose diameter decreases toward the axially forward end side, and flows to the outside through the second outer hole 176, which is the forward end opening of the taper wall 172, while maintaining the flow direction. As described above, through employment of the configuration for forcing the exhaust gas G to flow straight toward the second outer hole 176 and discharging it, the exhaust gas G can be discharged efficiently and smoothly.

Moreover, in the gas sensor 100 of the present embodiment, the entirety of the taper wall 172 is disposed on the axially forward end side in relation to the inner bottom wall 162 of the inner protector 161. Therefore, the exhaust gas G discharged from the second inner holes 166 of the second inner wall 165 of the inner protector 161 passes through the second space S2 between the second outer wall 175 and the second inner wall 165, enters the large in-taper space S4 surrounded by the taper wall 172 only (where the inner protector 161 does not exist), and then flows toward the second outer hole 176.

Figure 6:
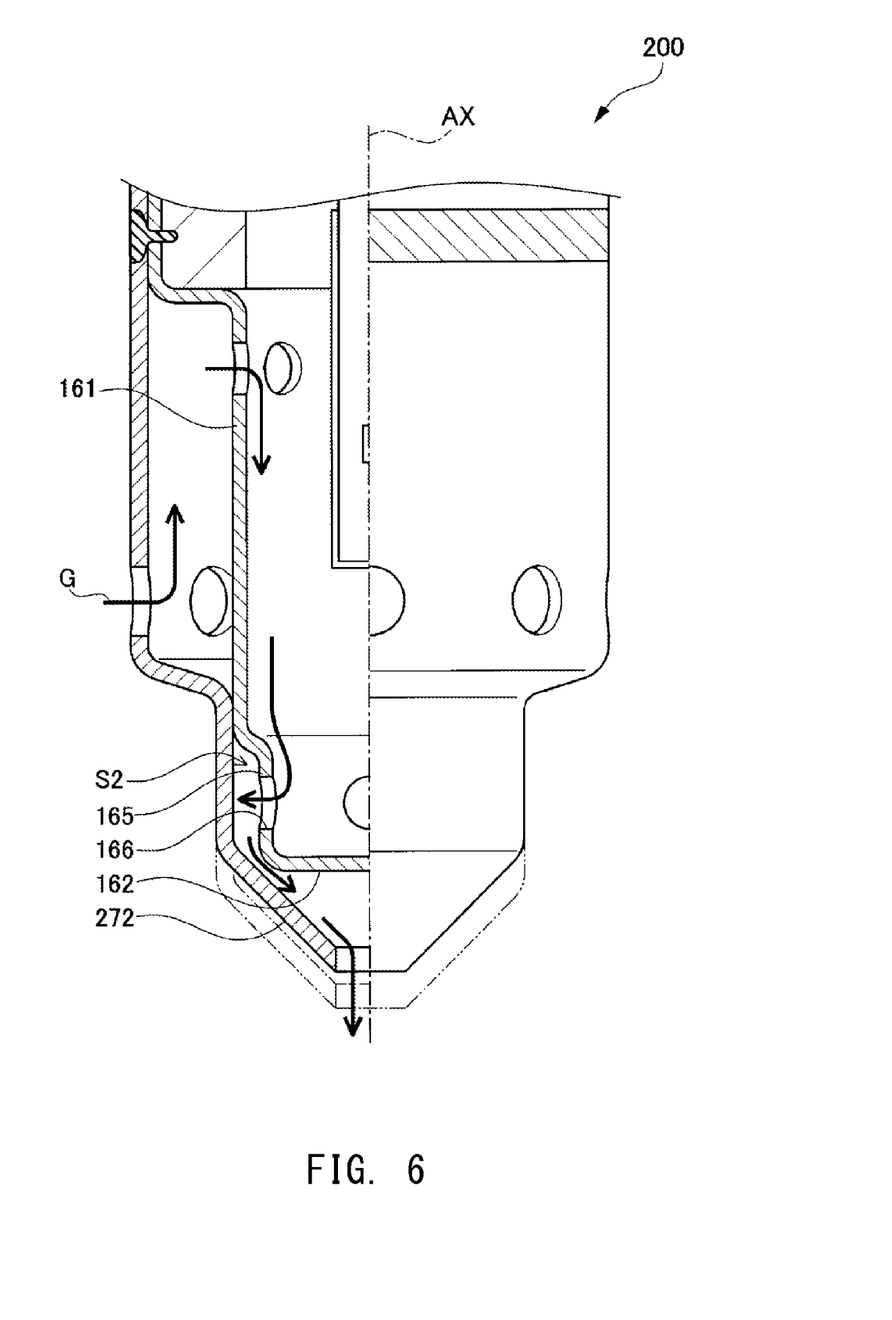
FIG. 6 View used for describing a flow of a gas-to-be-detected within a gas sensor of a comparative example.

FIG. 6 shows a gas sensor 200 of a comparative example. Unlike the gas sensor 100 of the embodiment, in the gas sensor 200, the taper wall 272 is disposed such that a portion (located on the base end side, the upper side in FIG. 6) of the taper wall 272 is located on the axially base end side (the upper side in FIG. 6) in relation to the inner bottom wall 162 of the inner protector 161. In other words, the gas sensor 200 differs from the gas sensor 100 of the embodiment in that the taper wall is moved toward the base end side such that a base-end-side portion of the taper wall is located on the axially base end side in relation to the inner bottom wall 162 of the inner protector 161. Notably, in FIG. 6, the position of the taper wall 172 of the embodiment is indicated by an alternate long and two short dashes line.

In the case of this gas sensor 200, the exhaust gas G discharged from the second inner holes 166 passes through the gap between the taper wall 272 and the second inner wall 165. Like the taper wall 172 of the embodiment, the taper wall 272 has the shape of a tapered tube whose diameter decreases toward the axially forward end side. Therefore, the space between the taper wall 272 and the second inner wall 165 in the gas sensor 200 is narrower than the second space S2 between the second outer wall 175 and the second inner wall 165 in the gas sensor 100 (see FIGS. 4 and 6). Therefore, in the gas sensor 200, the gas flow passage becomes narrower, and the gas discharge performance deteriorates.

In contrast, in the gas sensor 100 of the embodiment, the entire taper wall 172 is located on the axially forward end side in relation to the inner bottom wall 162 of the inner protector 161. Therefore, a large gas flow passage can be secured, whereby the gas discharge performance becomes good.

Accordingly, in the gas sensor 100 of the embodiment, the gas discharge performance becomes good, and as a result, the responsiveness of the gas sensor can be enhanced.

Figure 5:
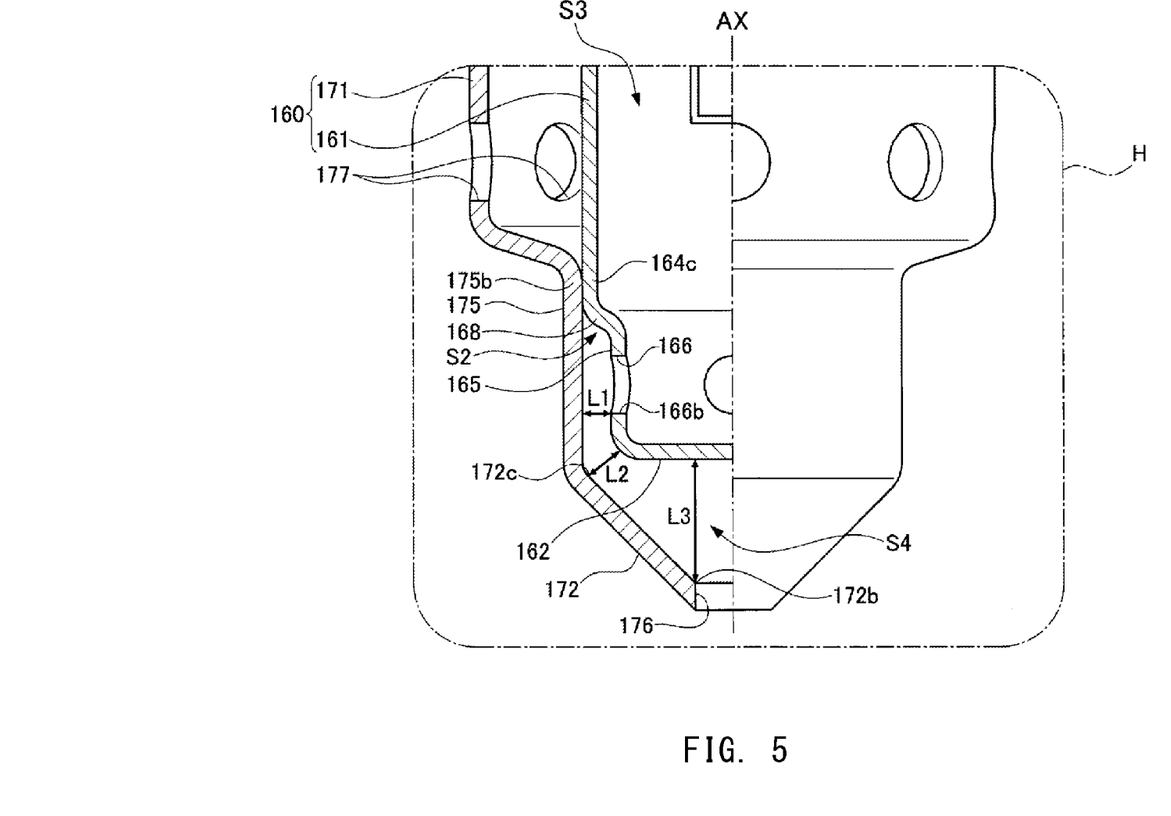
FIG. 5 Enlarged view of a portion H of FIG. 1.

Moreover, as shown in FIG. 5, in the gas sensor 100 of the embodiment, a relation L1<L2<L3 is satisfied, where L1 represents the shortest distance between the second outer wall 175 and the second inner wall 165 at the forward ends 166b of the second inner holes 166 (a portion of the second inner wall 165 located at a position corresponding to the forward ends 166b of the second inner holes 166), L2 represents the shortest distance between the base end 172c of the taper wall 172 and the inner protector 161, and L3 represents the shortest distance between the inner bottom wall 162 and the forward end 172b of the taper wall 172. As a result, the gas flow passage tends to expand from the second inner holes 166 of the inner protector 161 toward the second outer hole 176 of the outer protector 171. Therefore, the gas sensor 100 of the embodiment has a further improved gas discharge performance.

Incidentally, when water enters the interior of the outer protector 171 from the outside through the second outer hole 176 of the outer protector 171, the water may flow from the second outer hole 176 of the outer protector 171 toward the second inner holes 166 of the inner protector 161. However, since the gas sensor 100 of the embodiment satisfies the above-mentioned relation L1<L2<L3, the flow passage of the water tends to narrow from the second outer hole 176 of the outer protector 171 toward the second inner holes 166 of the inner protector 161. As a result, even when water enters the interior of the outer protector 171 from the outside through the second outer hole 176 of the outer protector 171, the water hardly flows into the second space S2, and hardly flows into the interior of the inner protector 161 through the second inner holes 166.

In the gas sensor of the above-described Patent Document 1 (Japanese Patent Application Laid-Open No. 2011-112557), a large diameter portion of the outer protector is located on the radially outer side of the forward end portion of the metallic shell. Further, a trunk portion which is smaller in diameter than the large diameter portion is disposed on the radially inner side in relation to the large diameter portion with a step portion which is bent radially inward being disposed therebetween. The trunk portion forms a space in cooperation with a trunk portion (corresponding to the first inner wall of the present invention) of the inner protector.

Meanwhile, in the gas sensor 100 of the embodiment, as shown in FIG. 4, the base end portion 174b of the first outer wall 174 is located on the radially outer side of the forward end fixing portion 113 of the metallic shell 110, and the first outer wall 174 has the shape of a tube (cylindrical tube) which extends straight from a position located on the radially outer side of the forward end fixing portion 113 of the metallic shell 110 toward the axially forward end side (the lower side in FIG. 4).

As described above, in the gas sensor 100 of the embodiment, unlike the gas sensor of Patent Document 1, the first outer wall 174 extends straight from the position located on the radially outer side of the forward end fixing portion 113 of the metallic shell 110 toward the axially forward end side without being bent toward the radially inner side. As a result, as compared with the case where the first outer wall 174 is bent toward the radially inner side, a larger gap can be formed between the first outer wall 174 and the first inner wall 164. Therefore, water entering the interior of the outer protector 171 through the first outer holes 177 can be stored in the gap in a large amount, and can be discharged through the first outer holes. As a result, even when water enters through the first outer holes 177, the water hardly reaches the first inner holes 167 and hardly flows into the interior of the inner protector 161 through the first inner holes 167. Accordingly, in the gas sensor 100 of the embodiment, water hardly adheres to the detection element 120.

Notably, in the present embodiment, the forward end fixing portion 113 of the metallic shell 110 corresponds to the "forward end portion of the housing" described in claims.

Furthermore, in the gas sensor 100 of the embodiment, the diameter D1 of a circle (or a sphere) inscribed to each first inner hole 167 (a wall surface which forms the first inner hole 167) is smaller than the diameter D2 of a circle (or a sphere) inscribed to each first outer hole 177 (a wall surface which forms the first outer hole 177) (see FIGS. 1 to 3). Notably, in the present embodiment, since the first inner holes 167 are circular, the diameter D1 of the inscribed circles (inscribed spheres) of the first inner holes 167 coincides with the diameter of the first inner holes 167. Further, since the first outer holes 177 are also circular, the diameter D2 of the inscribed circles (inscribed spheres) of the first outer holes 177 coincides with the diameter of the first outer holes 177.

The diameter D1 of the first inner holes 167 (the diameter D1 of the inscribed circles of the first inner holes 167) corresponds to the maximum diameter of water droplets which can pass through the first inner holes 167. Similarly, the diameter D2 of the first outer holes 177 (the diameter D2 of the inscribed circles of the first outer holes 177) corresponds to the maximum diameter of water droplets which can pass through the first outer holes 177. Accordingly, by making the diameter D1 of the first inner holes 167 smaller than the diameter D2 of the first outer hole 177, it becomes more difficult for water to pass through the first inner holes 167, as compared with the first outer holes 177. As a result, even when water has entered the interior of the outer protector 171 through the first outer holes 177, the water is less likely to flow into the interior of the inner protector 161 through the first inner holes 167. Accordingly, in the gas sensor 100 of the present embodiment, water is less likely to adhere to the detection element 120.

Further, as described above, in the gas sensor 100 of the present embodiment, the exhaust gas G introduced into the interior of the outer protector 171 from the outside through the first outer holes 177 of the outer protector 171 flows through the first inner holes 167 of the inner protector 161 into the internal space S3, then flows within the internal space S3 toward the axially forward end side (the lower side in FIG. 4), and is discharged to the outside of the inner protector 161 through the second inner holes 166 of the inner protector 161. The exhaust gas G is then discharged to the outside of the protector 160 through the second outer hole 176 of the outer protector 171.

Incidentally, the smaller the opening area of a hole, the greater the difficulty for the exhaust gas G to pass through the hole. Accordingly, of the second outer hole 176, the second inner holes 166, and the first inner holes 167, a hole(s) which has the smallest opening area (total opening area) determines the amount of the exhaust gas G discharged to the outside of the protector 160 (discharge performance).

In the gas sensor 100 of the embodiment, the total opening area A of the second outer hole 176, the total opening area B of the second inner holes 166, and the total opening area C of the first inner holes 167 satisfy the relation A<B<C. Namely, of the totals opening areas of the second outer hole 176, the second inner holes 166, and the first inner holes 167, the total opening area A of the second outer hole 176 is made smallest. Accordingly, in the gas sensor 100 of the embodiment, the amount of gas discharged to the outside of the protector 160 (discharge performance) is adjusted by the second outer hole 176 without being affected by the gas discharge performance of the second inner holes 166 and that of the first inner holes 167.

In addition, of the totals areas of the second outer hole 176, the second inner holes 166, and the first inner holes 167, the total opening area C of the first inner holes 167 is made largest. Therefore, the introduction of the exhaust gas G into the internal space S3 of the inner protector 161 through the first inner holes 167 becomes easier. As a result, the responsiveness of the gas sensor can be enhanced.

Notably, in the present embodiment, a plurality of (four) second inner holes 166 are formed. Accordingly, the "total opening area" of the second inner holes 166 is the sum of the opening areas of the second inner holes 166. This also applies to the first inner holes 167.

Furthermore, in the gas sensor 100 of the embodiment, the total opening area D of the first outer holes 177 and the total opening area C of the first inner holes 167 satisfy the relation C<D. Accordingly, in the gas sensor 100 of the embodiment, the total opening area A of the second outer hole 176, the total opening area B of the second inner holes 166, the total opening area C of the first inner holes 167, and the total opening area D of the first outer holes 177 satisfy the relation A<B<C<D. As described above, of the totals areas of the first outer holes 177, the first inner holes 167, the second inner holes 166, and the second outer hole 176, the total opening area D of the first outer holes 177 is made largest. Therefore, the introduction of the exhaust gas G into the interior of the protector 160 through the first outer holes 177 becomes easier. As a result, the responsiveness of the gas sensor can be enhanced.

Notably, in the present embodiment, a plurality of (eight) first outer holes 177 are formed. Accordingly, the "total opening area" of the first outer holes 177 is the sum of the opening areas of the first outer holes 177.

Moreover, in the gas sensor 100 of the embodiment, the connection wall 168, which connects the first inner wall 164 and the second inner wall 165 of the inner protector 161, has the shape of a tapered tube (truncated conical tube) whose diameter decreases toward the axially forward end side (see FIG. 4). As a result, as compared with the case where the connection wall has the shape of a flat ring extending orthogonally to the axis AX, the flow of the exhaust gas G which flows within the internal space S3 toward the axially forward end side (from the space surrounded by the first inner wall 164 to the space surrounded by the second inner wall 165) can be made smooth.

Also, in the gas sensor 100 of the embodiment, the forward end of the inner protector 161 (the forward end of the second inner wall 175) is closed by the inner bottom wall 162. Namely, the inner bottom wall 162 of the inner protector 161 does not have a through-hole which penetrates the inner bottom wall 162. As a result, the forward end opening (the second outer hole 176) of the taper wall 172 and the inner bottom wall 162 of the inner protector 161 overlap each other as viewed in the axial direction. Therefore, when external water enters the interior of the protector 160 through the second outer hole 176, which is the forward end opening of the taper wall 172, the inner bottom wall 162 of the inner protector 161 prevents the water from flowing directly into the interior of the inner protector 161. As a result, it is possible to properly protect the detection element 120 accommodated within the inner protector 161 from adhesion of water.

Further, in the gas sensor 100 of the embodiment, the first outer holes 177 are disposed at the forward end portion of the first outer wall 174, and the first inner holes 167 are disposed at the base end portion of the first inner wall 164. As a result, the first inner holes 167 can be greatly separated from the first outer holes 177 toward the axially base end side. Therefore, even when water enters through the first outer holes 177, the water becomes less likely to reach the first inner holes 167, and becomes less likely to flow into the interior of the inner protector 161 through the first inner holes 167. Therefore, the water becomes more unlikely to adhere to the detection element 120.

Although the present invention has been described on the basis of an embodiment thereof, the present invention is not limited to the embodiment. Needless to say, the present invention may be implemented while being properly modified without departing from the scope of the invention.

For example, in the embodiment, the gas sensor 100 is a full-range air/fuel ratio sensor. However, the present invention can be applied to oxygen sensors, $NO_x$ sensors, HC sensors, etc.

Also, in the present embodiment, the base end portion 175b of the second outer wall 175 and the forward end portion 164c of the first inner wall 164 are airtightly connected together by means of press-insertion (fitting) of the forward end portion 164c of the first inner wall 164 into the base end portion 175b of the second outer wall 175. However, the manner of airtightly connecting the base end portion of the second outer wall and the forward end portion of the first inner wall is not limited to fitting. For example, the base end portion of the second outer wall and the forward end portion of the first inner wall may be airtightly connected together by means of crimping or welding (welding over the entire circumference).

Furthermore, in the present embodiment, the number of the first outer holes 177 is 8, the number of the first inner holes 167 is 8, and the number of the second inner holes 166 is 4. However, the numbers of the first outer holes, the first inner holes, and the second inner holes may be freely set so as to satisfy the above-described relation among their total opening areas. Therefore, the embodiment may be modified such that the first outer holes, the first inner hole, and the second inner holes are rendered the same in number, and the opening area per hole of the first outer holes, that of the first inner holes, and that of the second inner holes are properly set so as to satisfy the above-described relation among their total opening areas.

DESCRIPTION OF REFERENCE NUMERALS

100: gas sensor
110: metallic shell (housing)
113: forward end fixing portion of the metallic shell (forward end portion of the housing)
120: detection element
121: detection portion
123: gas introduction portion
160: protector
161: inner protector
162: inner bottom wall
164: first inner wall
164c: forward end portion of the first inner wall
165: second inner wall
166: second inner hole
167: first inner hole
168: connection wall 171: outer protector
172: taper wall
174: first outer wall
175: second outer wall
175b: base end portion of the second outer wall
176: second outer hole
177: first outer hole
AX: axis
G: exhaust gas (gas-to-be-detected)
D1: diameter of the first inner holes (diameter of the inscribed circles of the first inner holes)
D2: diameter of the first outer holes (diameter of the inscribed circles of the first outer holes)
S1: first space
S2: second space
S3: internal space
S4: in-taper space

The invention claimed is:

1. A gas sensor comprising:
a detection element extending in an axial direction and having a detection portion which is provided on a forward end side thereof and adapted to detect a particular gas component contained in a gas-to-be-detected;
a housing which surrounds a radial circumference of the detection element in a state in which the detection portion projects from a forward end of the housing; and
a protector which is fixed to the housing and which surrounds the circumference of the detection portion, the protector including an inner protector which accommodates the detection portion in an internal space of the inner protector, and an outer protector which accommodates the inner protector, wherein
the inner protector includes
a tubular first inner wall having a first inner hole extending therethrough,
a tubular second inner wall which is located on an axially forward end side of the first inner wall and which has a diameter smaller than that of the first inner wall, the second inner wall having a second inner hole extending therethrough, and
an inner bottom wall which closes a forward end of the second inner wall; and
the outer protector includes
a tubular first outer wall which surrounds the circumference of the first inner wall and forms a tubular first space between the first outer wall and the first inner wall, the first outer wall having a first outer hole extending therethrough at a position on the axially forward end side in relation to the first inner hole,
a tubular second outer wall which is located on the axially forward end side of the first outer wall, which has a diameter smaller than that of the first outer wall and larger than that of the first inner wall, and which surrounds the circumference of the second inner wall and forms a tubular second space between the second outer wall and the second inner wall, the second outer wall being airtightly connected, at a base end portion thereof, to a forward end portion of the first inner wall, and extending toward the axially forward end side in relation to the inner bottom wall, and
a taper wall which is located on the axially forward end side of the second outer wall, which has the shape of a tapered tube whose diameter decreases toward the axially forward end side, and which has a second outer hole which is a forward end opening of the taper wall, the entirety of the taper wall being disposed on the axially forward end side in relation to the inner bottom wall.

2. A gas sensor as claimed in claim 1, wherein a relation $L1<L2<L3$ is satisfied, where L1 represents the shortest distance between the second outer wall and the second inner wall at a forward end of the second inner hole, L2 represents the shortest distance between a base end of the taper wall and the inner protector, and L3 represents the shortest distance between a forward end of the taper wall and the inner bottom wall.

3. A gas sensor as claimed in claim 1, wherein
a base end portion of the first outer wall is located on a radially outer side of a forward end portion of the housing; and
the first outer wall has a tubular shape and extends straight from a position located on the radially outer side of the forward end portion of the housing toward the axially forward end side.

4. A gas sensor as claimed in claim 1, wherein the diameter of an inscribed circle of the first inner hole is smaller than that of the first outer hole.

5. A gas sensor as claimed in claim 1, wherein a relation $A<B<C$ is satisfied, where A represents the total opening area of the second outer hole, B represents the total opening area of the second inner hole, and C represents the total opening area of the first inner hole.

6. A gas sensor as claimed in claim 5, wherein a relation $C<D$ is satisfied, where C represents the total opening area of the first inner hole, and D represents the total opening area of the first outer hole.

7. A gas sensor according to as claimed in claim 1, wherein
the inner protector has a connection wall for connecting the first inner wall and the second inner wall together; and
the connection wall has the shape of a tapered tube whose diameter decreases toward the axially forward end side.

8. A gas sensor as claimed in claim 1, wherein
the first outer hole is located at a forward end portion of the first outer wall; and
the first inner hole is located at a base end portion of the first inner wall.

* * * * *